United States Patent
Gomm

[19]

[11] Patent Number: 5,377,531
[45] Date of Patent: Jan. 3, 1995

[54] PORTABLE OIL CHANGE ANALYZER

[76] Inventor: Nelson R. Gomm, 14 Gioconda Ave., Acton, Mass. 01720

[21] Appl. No.: 129,865

[22] Filed: Sep. 30, 1993

[51] Int. Cl.$^6$ ............................................. G08B 21/00
[52] U.S. Cl. ................................. 73/53.05; 73/54.02; 340/457.4; 340/631
[58] Field of Search ................. 73/53.01, 53.05, 53.07, 73/54.02; 340/603, 457.4, 631

[56] References Cited

U.S. PATENT DOCUMENTS

| | | | |
|---|---|---|---|
| 3,526,127 | 5/1970 | Sarkis | 73/53.05 |
| 4,082,511 | 4/1978 | Bedford | 73/53.05 |
| 4,113,384 | 9/1978 | Lauer et al. | 356/70 |
| 4,281,533 | 8/1981 | Eesley et al. | 73/15 |
| 4,497,200 | 2/1985 | Tournier | 73/53.05 |
| 4,646,070 | 2/1987 | Yasuhara et al. | 340/603 |
| 4,742,476 | 5/1988 | Schwartz et al. | 364/550 |
| 4,785,287 | 11/1988 | Honma et al. | 340/631 |
| 4,970,492 | 11/1990 | King | 340/450.3 |
| 5,043,697 | 8/1991 | Ayabe et al. | 340/457.4 |
| 5,194,910 | 3/1993 | Kirkpatrick, Jr. et al. | 73/53.05 |

OTHER PUBLICATIONS

Wazer et al., "Viscosity and Fl;ow Measurement", Interscience Publishers, New York pp. 268, 269, 325, 326, 1963.

Primary Examiner—Hezron E. Williams
Assistant Examiner—Michael J. Brook

[57] ABSTRACT

A small sample of combustion engine lubrication oil is analyzed, simultaneously, for its viscosity and contamination level in a compact, self-contained, computer-controlled unit. If the combination of viscosity and contamination level falls outside of the acceptable range, which is determined by comparison to a digitally stored matrix of the various states of used motor oil, a warning is displayed recommending that the oil be changed.

9 Claims, 8 Drawing Sheets

PORTABLE OIL CHANGE ANALYZER

BACKGROUND

1. Field of Invention

This invention relates to an electromechanical means for analyzing the condition of combustion engine lubrication oil, and more particularly, to a method and apparatus for indicating when the engine oil should be changed.

2. Description of Prior Art

It is well known in the motor vehicle art that engine mechanical wear is dependent on the lubricating ability of the engine crankcase oil and that its lubricating ability degrades as the engine is operated over time. All vehicle manufacturers that offer combustion engines provide guidelines for determining when engine oil should be changed. There are generally two operating conditions, nominal and severe, which require long and short oil change intervals respectively. Those skilled in the art recognize that nominal engine operating conditions are defined as highway driving in moderate climatic conditions. Severe engine operating conditions are defined as stop-and-go driving, extended idling, short trips (under 4 miles) in freezing weather and trailer towing. Vehicle manufacturers have suggested that the oil be changed approximately every 7,500 miles while operating under nominal operating conditions and every 3,000 miles while operating under severe operating conditions.

Those skilled in the art recognize that the interpretation of engine operating conditions by a motor vehicle operator is inaccurate over extended periods and that the required oil change intervals could be as low as 1,000 miles and as high as 10,000 miles. In prior art, this determination was more accurately performed by directly sensing the engine oil temperature and accumulative RPM. In other prior art the capacitance of the oil is measured while the engine is operating. These prior art methods do not properly account for the effects on oil condition due to extreme climatic temperatures, ambient humidity, and normal engine wear. Most of these prior art methods incorporate on-engine apparatus which is generally too complex for installation by the average vehicle owner. Due to high cost and limited proven technology, these on-engine oil change analyzers will be available to a small segment of vehicle owners.

Those skilled in the art of lubrication know that the most reliable means for determining the condition of any oil is to analyze it directly. The quality factors of an oil sample taken from the crankcase would determine whether the oil has degraded beyond continued usage. It is well known in the art of lubrication that the methodology for accurately determining the quality of oil has been standardized. In addition, testing to these standards requires extensive laboratory analysis on large samples of used oil. However, there presently exists no convenient and low cost analyzer capable of estimating the basic quality factors of used motor oil; viscosity and contamination.

OBJECTS AND ADVANTAGES

Accordingly, the present invention provides a portable apparatus for measuring the degree of deterioration of engine lubrication oil and for indicating the results of the analysis. The present invention can be easily operated by the average vehicle owner and does not require the application of state-of-the-art technology. Those skilled in the motor vehicle art recognize that the most critical physical parameters which relate to the condition of oil are viscosity and contamination. The present invention simultaneously measures the viscosity and contamination level pertaining to a sample of the used crankcase oil, then electronically compares the measured values to empirically derived values stored in a computing machine. If the oil measurements fall outside of the acceptable ranges stored in memory, the display warns that the oil should be changed.

Further objects and advantages of this invention include; 1) extending the oil change cycle on nearly all vehicles which would considerably reduce our consumption of oil, 2) more accurately predict the deterioration of oil due to severe driving conditions, 3) account for accelerated oil degradation in older vehicle engines, and 4) to provide a means for consumer protection. Additional advantages of this invention are its ease of use, short analysis cycle time, small oil sample requirement, simplicity of manufacture and its portability.

DESCRIPTION OF THE INVENTION

Figure 1:
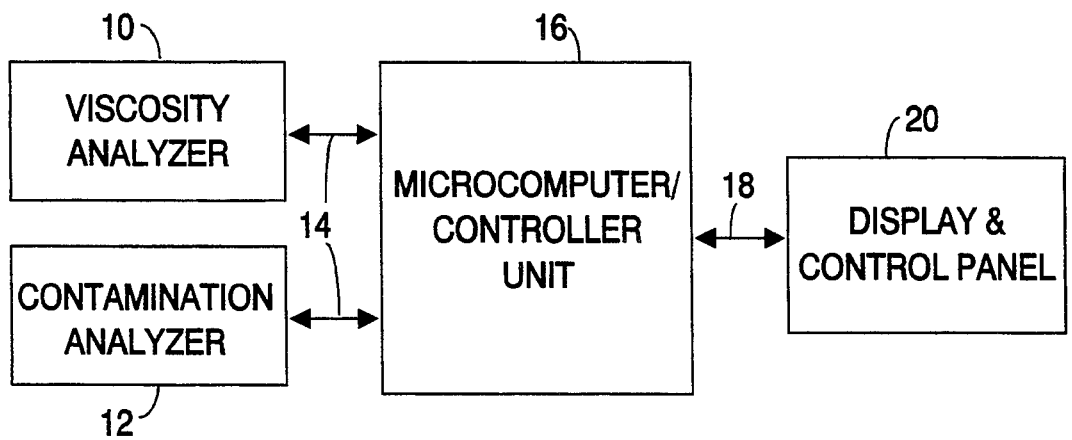
FIG. 1 is a block diagram representing the primary functions of this invention.

FIG. 1 illustrates the basic functional components of the present invention. A viscosity analyzer 10 and a contamination analyzer 12 are controlled by and provide signals to microcomputer/controller unit 16 via control and signal paths 14. A control and display panel 20 communicates with unit 16 via input and output path 18.

Figure 2:
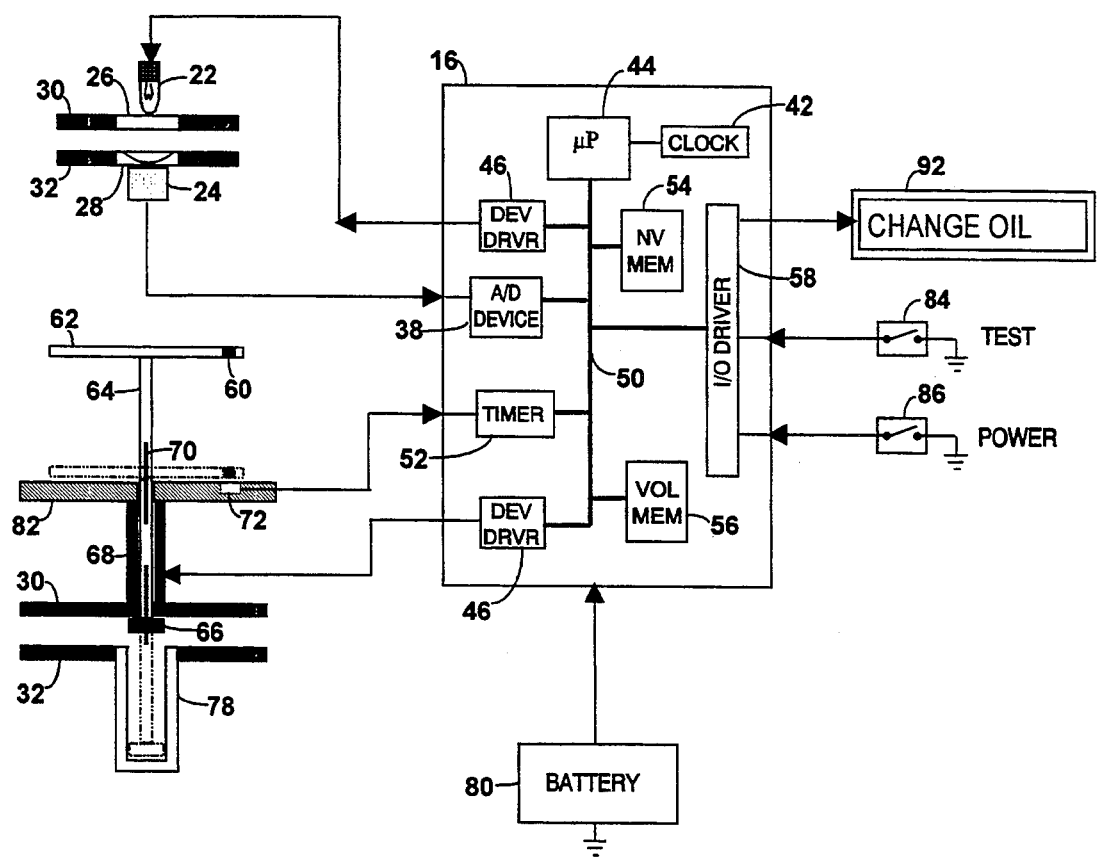
FIG. 2 is a schematic diagram of one emodiment of a portable oil change analyzer in accordance with the present invention.

FIG. 2 illustrates the preferred design embodiment of the present portable oil change analyzer. Contamination analyzer 12, from FIG. 1, comprises an illumination source 22, transparent panel 26, transparent concave dish 28 and light sensor 24. A small oil sample under test, deposited in dish 28, decreases the amplitude of light from source 22 which travels unattenuated through panel 26 and dish 28 and is measured by sensor 24. Panel 26 is embedded in the bottom surface 30 of upper housing 124 shown on FIG. 5. Dish 28 is embedded in the top surface 32 of lower housing 128 also shown on FIG. 5. Sensor 24 is directly below the bottom center of dish 28 and is isolated from all other sources of light. Electric current to source 22 is provided by device driver 46. The analog ouput from sensor 24 is digitized by analog-to-digital converter 38.

Viscosity analyzer 10, from FIG. 1, comprises a plunger assembly, solenoid 68, magnet-actuated switch 72 and oil sample receptacle 78. The plunger assembly consists of plunger shaft 64, plunger head 66 and plunger shaft travel stop 62 Shaft 64 moves vertically through solenoid 68 via a magnetic field acting on embedded shaft magnet 70. At the bottom of the plunger travel, as shown by phantom lines, magnet 60, which is embedded in stop 62, effects control over switch 72 Switch 72, which is embedded in plunger assembly support 82, provides a signal to timer 52 Electric current to energize solenoid 68 is provided by a second device driver 46. Depending on the direction of current to solenoid 68, the resulting magnetic field will retract or insert plunger head 66 into receptacle 78 Receptacle 78 is suspended from surface 32 and is removable for ease of cleaning or replacement. Head 66 and attached shaft 64 extent from surface 30 and move through the oil sample under analysis in receptacle 78 until stop 62 contacts support 82.

Microcomputer/controller unit 16, from FIG. 1, consists of microprocessor 44, clock 42, non-volatile memory 54, volatile memory 56, converter 38, timer 52, device drivers 46, input and output (I/O) driver 58, and data and control bus 50. Microprocessor 44 provides program execution and coordinated control of all unit 16 functions via bus 50. Non-volatile memory 54 permanently stores all executable program sequences and tabular data. Volatile memory 56 provides temporary storage for the data interpolation computations related to the oil sample being analyzed. I/O driver 58 drives digital display 92 and senses the status of power switch 86 and test switch 84. Digital display 92 could be a liquid crystal display (LCD). Battery 80 provides electrical power to all the devices including microcomputer 16.

Figure 3A:
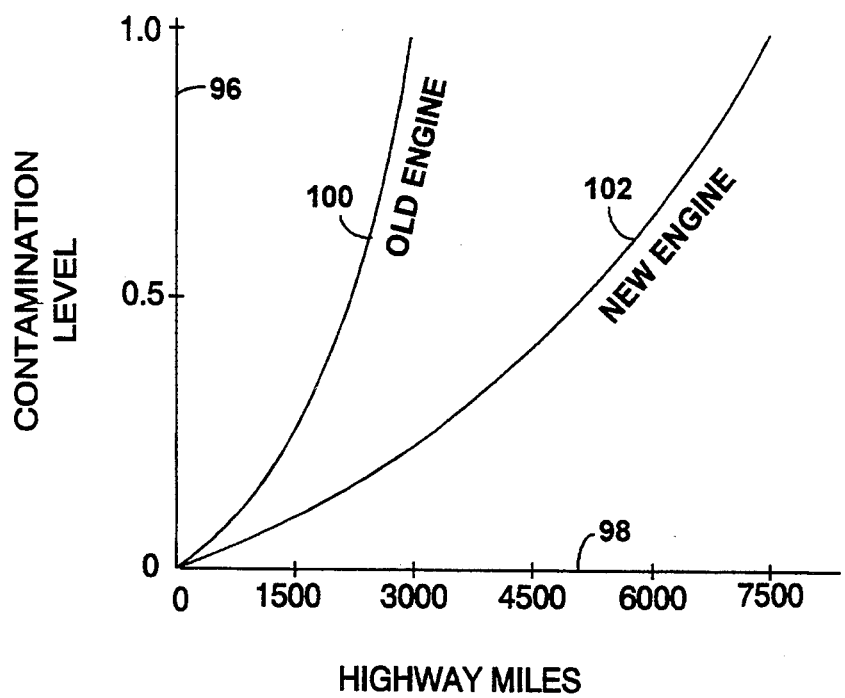
FIG. 3A is a graph correlating the contamination of engine oil to vehicle mileage.

FIG. 3A graphically shows the increase of the particulate and soluble opaque contamination in normally filtered engine oil as a function of vehicle miles driven under nominal operating conditions. Curve 102 indicates the average oil contamination rate for vehicle engines under 20,000 miles. Curve 100 indicates the average oil contamination rate for vehicle engines with 80,000 miles or more. It can be seen by comparing curve 102 to 100 that older vehicle engines accumulate contamination at a faster rate than newer vehicle engines. This is an indirect result of normal wear to high friction parts such as the cylinder walls, piston rings, and valve guides. This allows greater quantities of oil to enter the combustion chamber, incomplete burning of the fuel, and more combustion products to enter the oil pan. The maximum contamination level for newer engines at 7,500 miles was normalized to 1.0 producing contamination level scale 96. The engine oil samples were taken at equal intervals along highway mileage scale 98

Figure 3B:
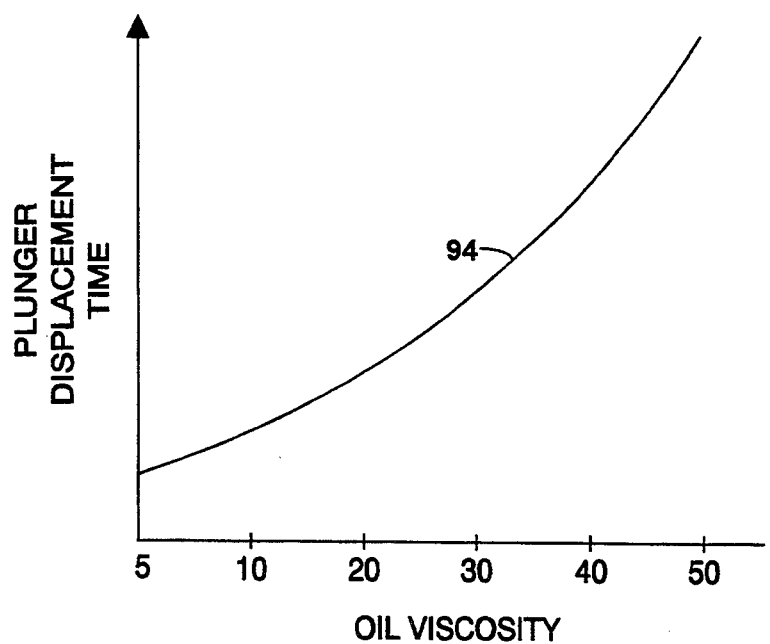
FIG. 3B is a graph correlating the viscosity of engine oil to plunger displacement time.

FIG. 3B, curve 94, shows the relationship of the plunger assembly vertical displacement time through engine oil of known viscosities near room temperature.

Figure 4:
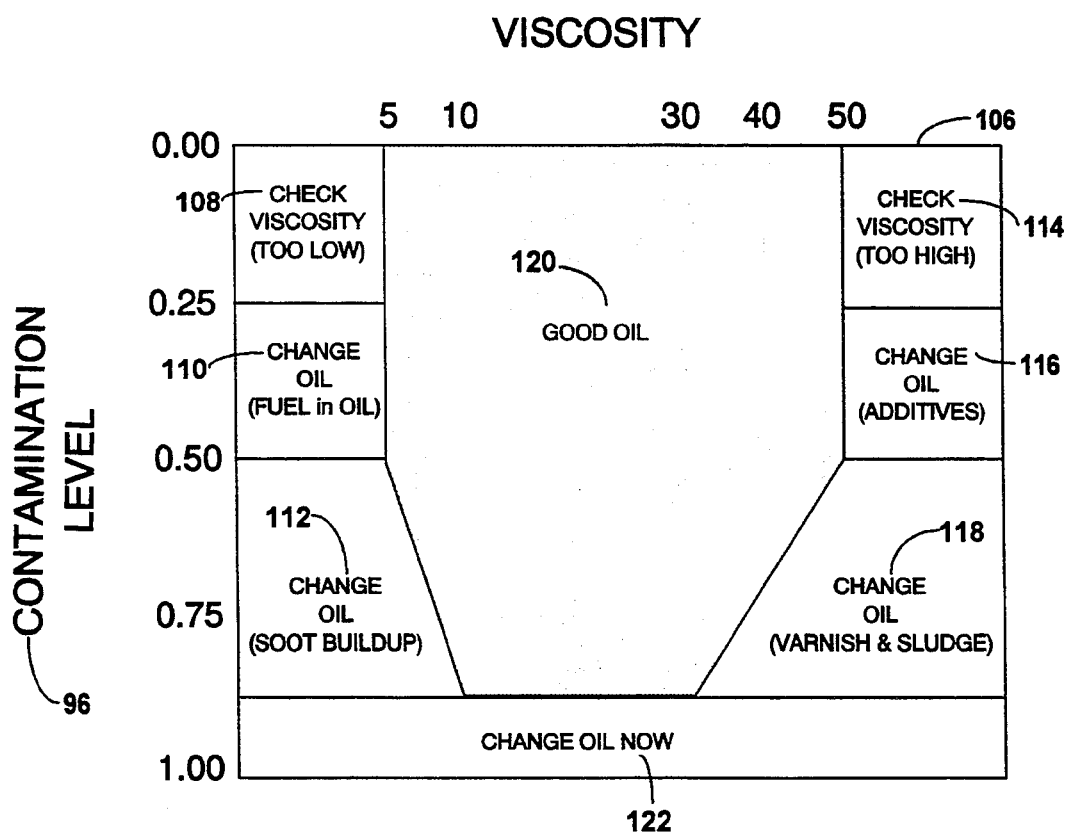
FIG. 4 is a two dimensional chart depicting the various states of used motor oil based on empirically derived viscosity and contamination data.

FIG. 4 depicts a matrix chart that combines the measurements of contamination and viscosity to produce various states of used engine lubrication oil. Viscosity scale 106 extends beyond the nominal range of engine oil viscosities used in hot and cold climates. Contamination level 96 corresponds to the normalized scale shown on FIG. 3A. Each area on the matrix chart is identified with a corresponding oil condition message that would appear on display 92 as a result of the oil analysis. CHECK VISCOSITY (TOO LOW) message 108 would indicate that, although the oil sample is relatively clean, the viscosity is lower than nominal. This could result from using a low viscosity oil that is out of tolerance or from coolant leaking into the lubrication system. CHANGE OIL (FUEL IN OIL) message 110 would indicate that the viscosity of the oil being sampled is below nominal and that it is most likely contaminated with fuel leaking into the lubrication system. CHANGE OIL (SOOT BUILDUP) message 112 would indicate that the oil sample is dirty and that the viscosity is dangerously low. This generally results from engine combustion with a rich fuel mixture. There is an increasing penalty on the minimum nominal viscosity as the contamination level increases. CHECK VISCOSITY (TOO HIGH) message 114 would indicate that, although the oil sample is relatively clean, the viscosity exceeds nominal values. This could result if excess viscosity enhancers have been added to the oil or if oil beyond nominal viscosity has been added to the crankcase. CHANGE OIL (ADDITIVES) message 116 would indicate that the viscosity of the sampled oil exceeds nominal and that a significant quantity of viscosity enhancing additive is present. CHANGE OIL (VARNISH & SLUDGE) message 118 would indicate a significant buildup of particulate and soluble contaminants. As the contamination level increases, a penalty is applied that decreases the maximum allowed viscosity. This is due to the thickening effect of the suspended varnish and sludge. CHANGE OIL NOW message 122 would indicate that the contamination level of the sampled oil has exceeded the allowable nominal value regardless of viscosity. Continued engine operation with oil in this condition will suffer decreased oil circulation due to sludge-clogged oil channels, excessive local friction due to surface contamination from varnish deposits and much higher oil temperatures due to diminished heat transfer capacity and flow characteristics. GOOD OIL message 120 will be displayed when the oil sample analysis results in nominal combinations of viscosity and contamination levels.

Figure 5:
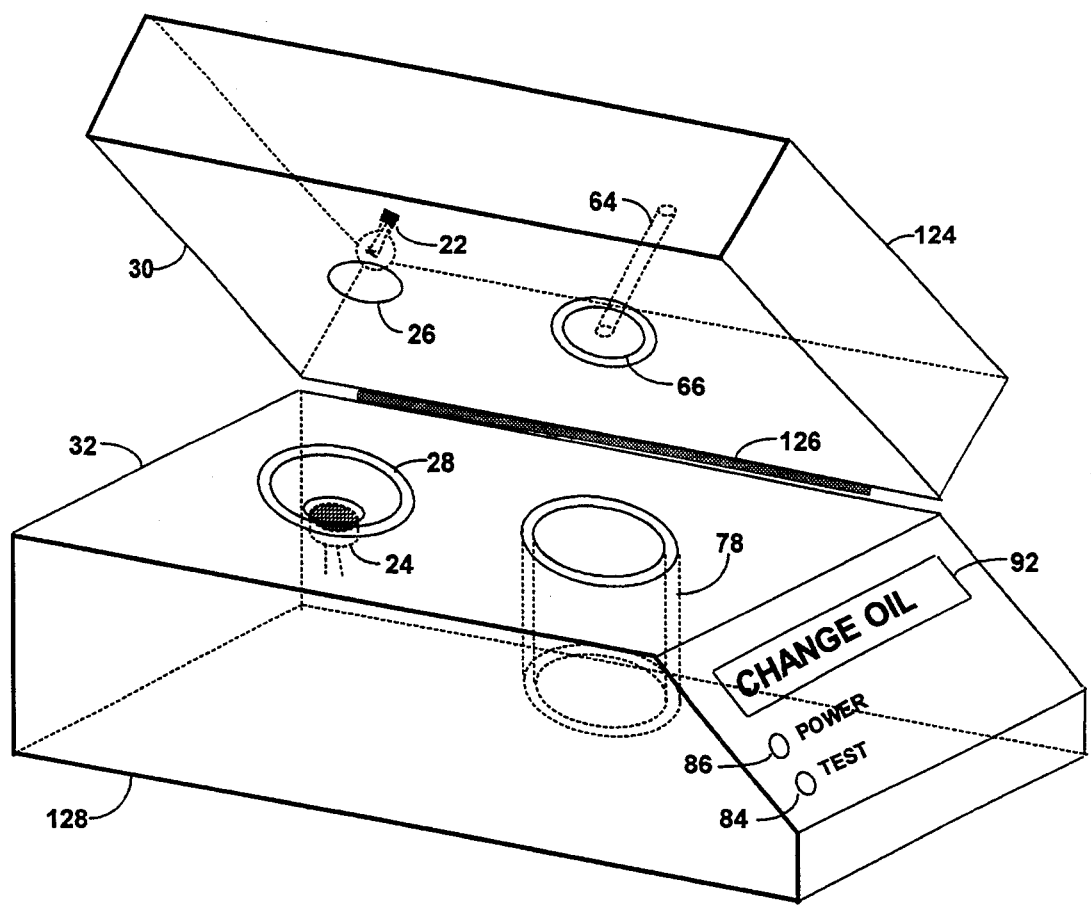
FIG. 5 is a three dimensional drawing of one proposed design of this invention which shows the means for accessing the oil sample volumes (open).

FIG. 5 illustrates one embodiment of the portable oil change analyzer. All analyzer components are contained in either upper housing 124 or lower housing 128. Hinge 126 allows housing 124 to be rotated open providing direct access to dish 28 and receptacle 78 for depositing and then removing the oil sample. Display 92 and switches 84 and 86 are accessible during all stages of operation.

Figure 6:
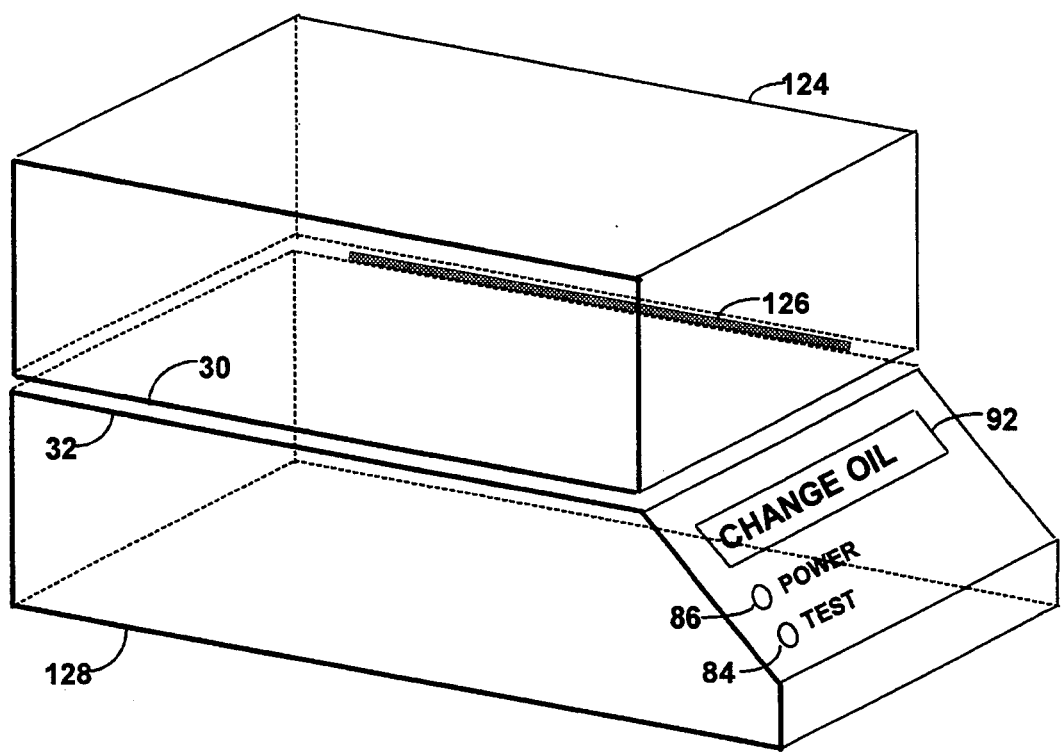
FIG. 6 is a three dimensional drawing depicting the invention in either storage or analysis mode (closed).

FIG. 6 further illustrates the embodiment described in FIG. 5 by showing it in either a test or storage configuration. Housing 124 is rotated closed such that surfaces 30 and 32 are parallel and nearly contacting each other. Although not explicitly shown in this closed configuration (refer to FIG.5), the light from source 22 is directly above and closest to sensor 24 and plunger head 66 is directly over receptacle 78. Variations of this embodiment would include separately accessible oil test sample volumes, a fully removable upper housing assembly, various types and locations for the display and switches, and non-rectangular housing geometry.

Figure 7:
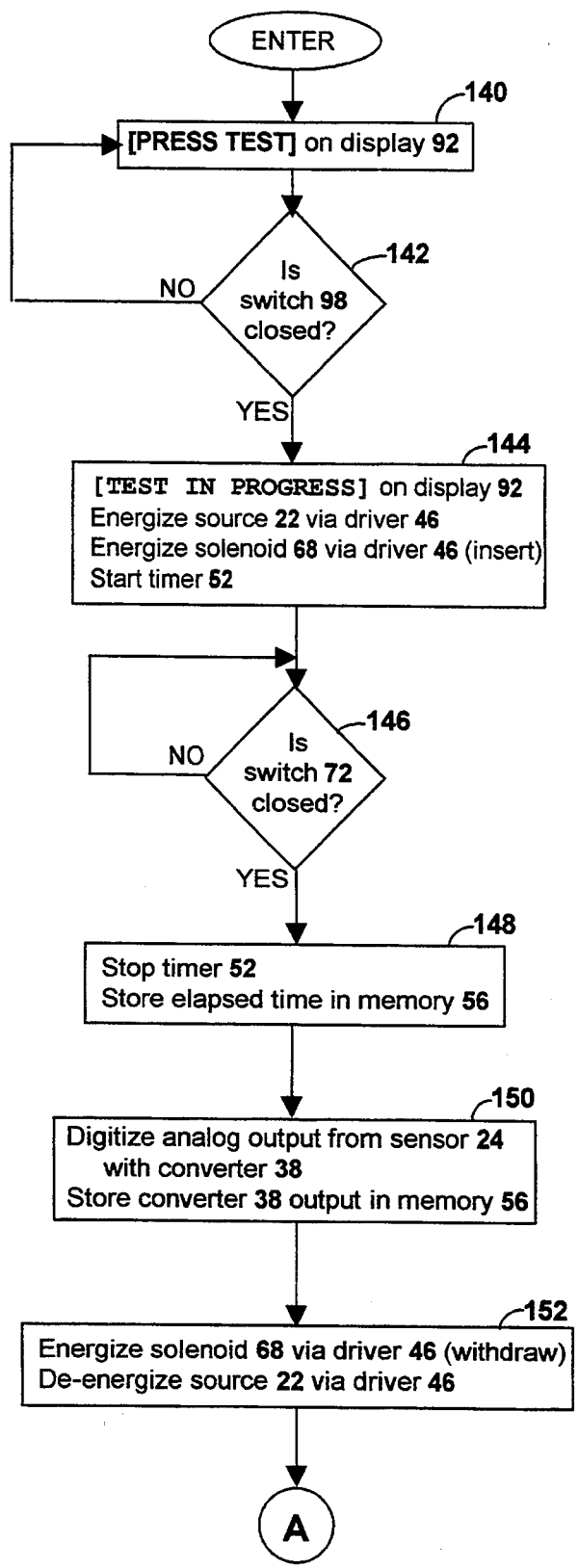
FIG. 7 is a logic flow diagram depicting the basic sequence of steps executed by the microcomputer for performing the oil change analysis.
Figure 7:
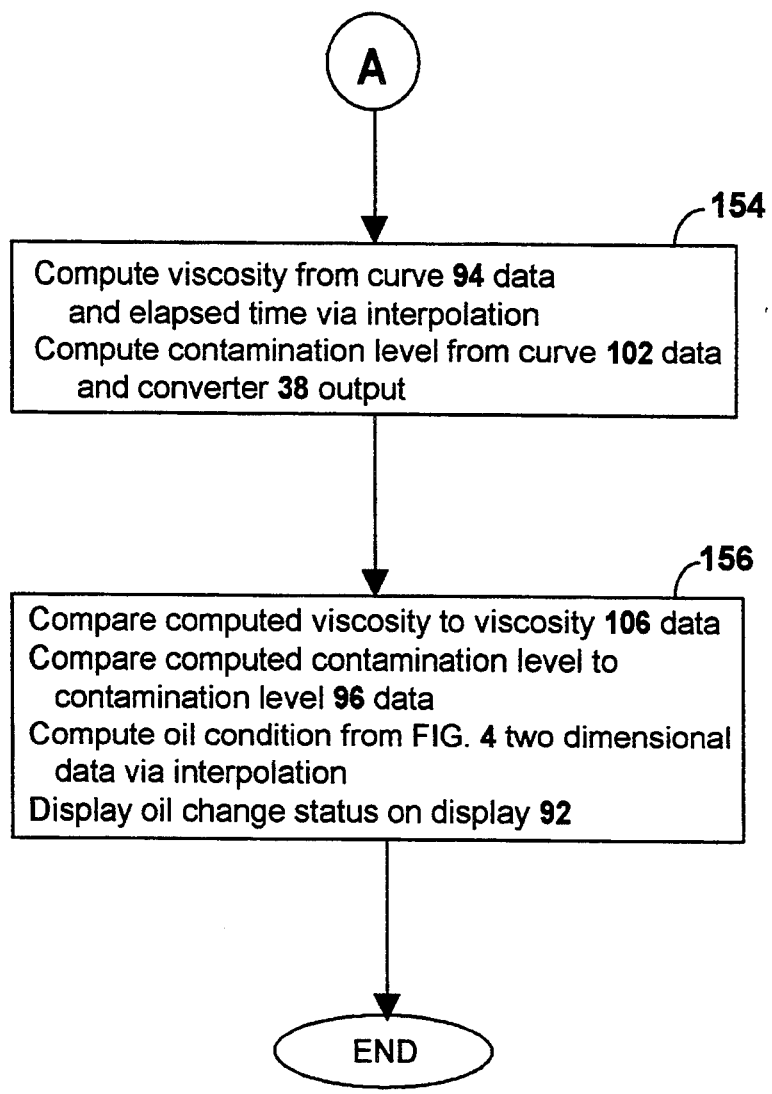

FIG. 7 depicts a flow diagram of the primary program instructions that are stored in memory 54 and executed by microprocessor 44. Not explicitly shown are the analyzer self-test program sequences and user prompts that provide instructional guidance in preparing the oil samples for testing. After successful completion of the self-test and all test preparations are completed, block 140 is executed and indicates PRESS TEST on display 92. Decision block 142 is cycled until switch 84 is closed enabling block 144 test sequences to begin. Decision block 146 is cycled until magnetic switch 72 closes indicating that the plunger assembly has reached the end of its travel. This also enables the execution of block 148 to complete the viscosity test by storing the elapsed time into memory 56. Block 150 then executes to complete the contamination test by storing the digitized output from sensor 24 into memory 56. Microprocessor 44 then executes block 152 to shut down the test assemblies. Block 154 then executes to convert the raw test data stored in memory to viscosity and contamination level based on empirical data stored in memory 54. Block 156 executes the logic that mathematically compares the measured values to those stored in memory 54 for the oil condition chart shown on FIG. 4. The pair of measured values will always map to one of the oil condition chart areas. Finally, block 158 executes to drive display 92 to indicate the condition of the oil, and in particular, whether or not it should be changed.

OPERATION OF THE INVENTION—FIGS. 5, 6, 7

The use and application of the portable oil change analyzer requires one to first place the base of housing 128 of the analyzer on a level surface. The analyzer is initially closed as shown in FIG. 6. Next, one turns the analyzer on by closing power switch 86. The analyzer then automatically performs a series of self tests to determine if it will perform properly. During this time, the analyzer will report the status of the self testing and, finally, its operational status on display 92. Assuming a successful self test outcome, the analyzer will next guide one through the steps required to properly deposit the oil samples into dish 28 and receptacle 78. This requires that the analyzer be opened as shown in FIG. 5. When one has completed depositing the oil samples, the analyzer is then closed as shown in FIG. 6 and indicates PRESS TEST on display 92. One then initiates the automated test sequence described in FIG. 7 by closing switch 84. At the end of testing, the analyzer will report the oil change status on display 92. One is next guided through a series of steps on display 92 that describe the oil sample removal and general cleaning process. The analyzer must be opened as shown in FIG. 5 to provide access to the oil samples. Since the amount of oil required for sampling is insignificant relative to the 4 to 5 quarts of oil generally required in a vehicle crankcase, many samples may be taken without affecting lubrication performance. Thus, one has the option of either reusing the oil sample by returning it to the crankcase or properly disposing of it. Finally, when the analyzer is cleaned and returned to the closed position, as shown in FIG. 6, it is ready for storage.

SUMMARY OF THE INVENTION

There is provided, in accordance with the present invention, a self-contained apparatus for analyzing the condition of combustion engine lubrication oil. The apparatus comprises first of a viscosity measurement device which provides a time delay for the displacement of a plunger through an oil sample in proportion to its viscosity. A second measurement apparatus comprising a light source above and a light sensitive element below a transparent oil sample dish, that operate in conjunction to generate an output that is inversely proportional to the quantity of light-attenuating contaminants present in the oil sample. A third apparatus comprises a computing machine which converts the measured time delay to a viscosity and the sensor output to a contamination level through the use of internally stored tables. This present computing apparatus then determines if the combined measurements of viscosity and contamination level are within acceptable limits by comparing them to an internally stored matrix of empirically derived used oil data. The fourth apparatus is provided to indicate the condition of the sampled oil and to warn that, if warranted, it should be changed.

Although this invention has been described in reference to the illustrated embodiment, various modifications thereto will occur to those skilled in the art. For example, a single oil sample receptacle may be used to perform both the viscosity and contamination analysis while employing similar principles of measurement; the display may be a matrix of light-emitting-diodes instead of a digital display device such as a liquid crystal display; the shape of the housing assemblies may be cylindrical instead of rectangular. In this regard, it will be understood that analyzers incorporating such modification may fall within the scope of this invention, which is defined by the appended claims and their legal equivalents, rather than by the example given.

What is claimed is:

1. An apparatus for determining the lubricating characteristics of combustion engine lubrication oil, said apparatus comprising a viscosity measuring element and a contamination measuring element, said viscosity measuring element comprising a plunger assembly and an oil sample receptacle, said plunger assembly comprising a plunger means, a solenoid means and a switch means for measuring a displacement time of said plunger through oil in said oil sample receptacle, said contamination measuring element comprising a light source and a light sensor operable to optically measure the variance in transmittance of light through an oil sample dish between said light source and said light sensor;

a calculating element, electronically connected to said viscosity measuring element and said contamination measuring element, comprising a processor means, a memory storage means, and a program means for conversion of said displacement time to a viscosity and the output from said light sensor to a normalized contamination level, and for correlating said viscosity and said contamination level to a state of oil degradation.

2. The apparatus of claim 1, wherein said plunger comprises a plunger head, a vertical shaft connected normally to said plunger head, and a magnet, embedded in said vertical shaft which passes through said solenoid.

3. The apparatus of claim 2, wherein said solenoid is capable of a reversible electromagnetic field in order to insert and withdraw the plunger via interaction with said magnet embedded in said vertical shaft.

4. The apparatus of claim 1, wherein said oil sample dish between said light source and said light sensor is transparent and is made of concave scratch-resistant polycarbonate, plastic, or glass.

5. The apparatus of claim 1, wherein said oil sample receptacle is removable for cleaning or replacement.

6. The apparatus of claim 1, wherein said processor interfaces with a display processor which drives a digital display indicating the state of the sampled oil.

7. The apparatus of claim 1, wherein said light source emits white light in the visible spectrum through a transparent panel means to protect said light source from damage and contamination.

8. The apparatus of claim 7, wherein said transparent panel is made of scratch-resistant polycarbonate, plastic, or glass.

9. The apparatus of claim 1, wherein an empirically-determined oil degradation matrix resides in said memory storage, comprising multiple states of used engine lubrication oil as a two dimensional function of viscosity and normalized contamination level, and said program means and said processor means are operable to correlate said viscosity and said contamination level from the oil samples to a state on the oil degradation matrix.

* * * * *